US007834062B2

(12) United States Patent
Dorn et al.

(10) Patent No.: US 7,834,062 B2
(45) Date of Patent: Nov. 16, 2010

(54) AMINOALKYLPHENOLS, METHODS OF USING AND MAKING THE SAME

(75) Inventors: Conrad P. Dorn, Plainfield, NJ (US); Mary Ann Powles, Freehold, NJ (US); Thomas F. Walsh, Watchung, NJ (US); Matthew J. Wyvratt, Mountainside, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/540,445

(22) Filed: Aug. 13, 2009

(65) Prior Publication Data

US 2009/0298949 A1    Dec. 3, 2009

Related U.S. Application Data

(62) Division of application No. 10/511,661, filed as application No. PCT/US03/19393 on Jun. 20, 2003, now Pat. No. 7,589,127.

(60) Provisional application No. 60/391,361, filed on Jun. 24, 2002.

(51) Int. Cl.
*A61K 31/135* (2006.01)
(52) U.S. Cl. ........................ 514/648; 514/649; 514/650; 514/654; 514/655; 564/337; 564/366; 564/373; 564/374; 564/381; 564/382; 564/390
(58) Field of Classification Search ................ 564/337, 564/366, 373, 374, 381, 382, 390; 514/648, 514/649, 650, 654, 655
See application file for complete search history.

(56) References Cited

U.S. PATENT DOCUMENTS 3,794,734 A    2/1974    Cragoe et al.

7,589,127 B2    9/2009    Dorn et al.

OTHER PUBLICATIONS

Berge et al. "Pharmaceutical Salts", Journal of Pharmaceutical Sciences, 1977, vol. 66, pp. 1-19.
Burckhalter et al. "Aminoalkylphenols as Antimalarials. I. Simply Substituted α-Aminocresols", Journal of the American Chemical Society, 1946, Vol. 68, pp. 1894-1901.
Duncan et al. "2-(ω-Aminoalkyl)-4-t-butyl-6-phenylphenols as Antimalarial Agents", Journal of the American Chemical Society, 1969, vol. 12, pp. 711-712.
Finn et al. Chemical Abstracts, 1951, 45:49820.
Provent et al. "Double Wittig Reactions with 4-Carboxybutylidene Triphenylphosphorane as the Key Step in the Synthesis of Benzene Derivatives Metadisubstituted with ωω'-Difunctionalized Six-Carbon Chains", Tetrahedron Letters, 1996, vol. 37, pp. 1393-1396.
Schmidt et al. "Antimalarial Activities of WR-194,965, an α-Amino-o-Cresol Derivative", Antimicrobial Agents and Chemotherapy, 1978, Vol. 14, pp. 672-679.
Stokker et al. "2-(Aminomethyl)phenols, a New Class of Saluretic Agents. 1. Effects of Nuclear Substitution", Journal of the American Chemical Society, 1980, vol. 23, pp. 1414-1427.
Zhang et al. "Base and Cation Effects on the Suzuki Cross-Coupling of Bulky Arylboronic Acid with Halopyridines: Sythesis of Pyridylphenols", Journal of Organic Chemistry, 1998, vol. 63, pp. 6886-6890.

*Primary Examiner*—Peter G O'Sullivan
(74) *Attorney, Agent, or Firm*—Kenneth R. Walton; Sheldon O. Heber; Sylvia A. Ayler

(57) ABSTRACT

The present invention relates to Mannich base antimalarial aminoalkylphenol compounds and their use against protozoa of the genus *Plasmodium*, particularly emerging strains of drug-resistant Plasmodia. This invention further relates to compositions containing such compounds and a process for making the compounds. This and other aspects of the invention are realized upon review of the entire specification.

10 Claims, No Drawings

AMINOALKYLPHENOLS, METHODS OF USING AND MAKING THE SAME

CROSS-REFERENCE TO RELATED APPLICATIONS

This application is a divisional of U.S. application Ser. No. 10/511,661, filed Oct. 18, 2004, now U.S. Pat. No. 7,589,127, which is the National Stage of International Application No. PCT/US2003/019393, filed Jun. 20, 2003, which claims the benefit under 35 U.S.C. 119(e) of U.S. Provisional Application No. 60/391,361, filed Jun. 24, 2002.

BACKGROUND OF THE INVENTION

Historically, malaria infections were controlled with quinoline-based alkaloids from the cinchona tree, particularly quinine. Insufficient supplies of quinine and the need to protect troops fighting in malaria-endemic regions fueled researchers to discover synthetic quinoline-based antimalarial agents. This effort led to a series of antimalarial compounds including chloroquine which has been the mainstay of antimalarial therapy since its introduction in 1945. Parallel medicinal chemistry efforts in the 1940s led to clinical evaluation of several phenolic Mannich bases as potential malarial agents.

However, the emergence of drug resistant strains of *Plasmodium* has caused many of the safest and least expensive antimalarial drugs to lose their effectiveness in many areas of the world. Therefore, there is a continued need to discover and develop antimalarial agents that are effective against new and old strains of *Plasmodium*.

The present invention relates to aminoalkylphenols, compositions containing an aminoalkylphenol as the active ingredient and methods of treating malaria. The compounds of this invention are antiprotozoal agents effective in vivo and in vitro against protozoa of the genus *Plasmodium* (*P. falciparum*, *P. bergei*, etc.), the infectious agent responsible for malaria. The compounds of this invention are phenolic Mannich base derivatives, a class of chemical substances that have been intensely studied for many years for their antimalarial properties. See Burckhalter, J. H., et al., *J. Am. Chem. Soc.*, 1946 Vol. 68, 1894-1901, and 1948, Vol. 70, 1363-1373, Duncan, W. G., et al., J. Med. Chem. 1969, 12, 711-112, and F. Y. Wiselogle, Ed.; *Survey of Antimalarial Drugs*, 1941-1945, Vols. I and II, Edwards Bros., Ann Arbor, Mich. Aminoalkylphenols are also discussed U.S. Pat. No. 3,794,734, issued Feb. 26, 1974 and Stokker, G. E., et al., *J. Med. Chem.* 1980, 23, 1414-27.

SUMMARY OF THE INVENTION

The present invention relates to Mannich base antimalarial aminoalkylphenol compounds and their use against protozoa of the genus *Plasmodium*, particularly emerging strains of drug-resistant Plasmodia. This invention further relates to compositions containing such compounds and a process for making the compounds. This and other aspects of the invention are realized upon review of the entire specification.

DETAILED DESCRIPTION OF THE INVENTION

In accordance with the present invention there are disclosed aminoalkylphenol compounds having structural formula I:

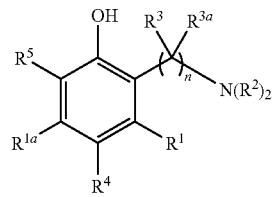

wherein, $R^5$, $R^{1a}$ and $R^1$ independently are hydrogen, $C_{1-6}$ alkyl halo, $C_{1-6}$ alkoxy, $C_{3-10}$ cycloalkyl, $C_{6-10}$ aryl, and trihalovinyl, said aryl optionally substituted with 1-3 groups of $R^a$;

$R^2$ is hydrogen, $C_{1-6}$ alkyl, and $C_{3-10}$ cycloalkyl; taken together with any intervening atoms can form a 3 to 7 membered carbocyclic or heterocyclic ring saturated or unsaturated, said heterocyclic ring containing 1-2 heteroatoms independently chosen from O, C(O), S, SO, $SO_2$, N, or $NR^{2a}$ and optionally substituted by 1-3 Ra groups;

$R^{2a}$ is hydrogen, and $C_{1-6}$ alkyl;

$R^3$ and $R^{3a}$ are independently hydrogen, halo, $C_{1-6}$ alkyl, $C_{3-10}$ cycloalkyl, and $C_{6-10}$ aryl, said aryl and alkyl optionally substituted with 1-3 groups of $R^a$; or $R^3$ and $R^{3a}$ taken together with any intervening atoms can form a 3 to 7 membered carbocyclic or heterocyclic ring saturated or unsaturated, said heterocyclic ring containing 1-2 heteroatoms independently chosen from O, C(O), S, SO, $SO_2$, N, or $NR^{2a}$ and optionally substituted by 1-3 $R^a$ groups;

$R^4$ is hydrogen, halo, $C_{1-6}$ alkyl, and trihaloalkyl;

$R^a$ represents $C_{1-6}$ alkoxy, $C_{1-6}$ alkyl, $CF_3$, nitro, amino, cyano, $C_{1-6}$ alkylamino, or halogen; and n represents 1-3;

or a pharmaceutically acceptable salt, enantiomer, or diasteriomer thereof.

In one embodiment of this invention $R^{1a}$ and $R^1$ independently are hydrogen, tert-butyl, 1,2,2-trichlorovinyl, phenyl, and all other variables are as originally described.

In another embodiment of this invention $R^2$ is hydrogen or $C_{1-4}$ alkyl, n is 1 and all other variables are as originally described.

In still another embodiment of this invention $R^{1a}$ and $R^1$ independently are hydrogen, tert-butyl, 1,2,2-trichlorovinyl, or phenyl;

$R^2$ is hydrogen or $C_{1-4}$ alkyl, n is 1 and all other variables are as originally described.

Particular novel compounds of structural formula I which may be employed in the methods, uses and compositions of the present invention, include:
(1) 2-aminomethyl-5-tert-butyl-3-phenylphenol
(2) 2-aminomethyl-5-tert-butyl-3-(4-methylphenyl)phenol
(3) 3,5-di-tert-butyl-2-[(ethylamino)methyl]phenol
(4) 3,5-di-tert-butyl-2-[1-(ethylamino)ethyl]phenol
(5) 3,5-di-tert-butyl-2-[(methylamino)methyl]phenol
(6) 3,5-bis(trichlorovinyl)-2-[(ethylamino)methyl]phenol
(7) 3,5-di-tert-butyl-2-[(propylamino)methyl]phenol
(8) 2-[(ethylamino)methyl]-5-(trichlorovinyl)phenol
(9) 3,5-di-tert-butyl-2-[(butylamino)methyl]phenol
(10) 3,5-di-tert-butyl-2-[(cyclohexylamino)methyl]phenol
(11) 3,5-di-tert-butyl-2-[hexylamino)methyl]phenol

(12) 3,5-di-tert-butyl-2-[(octylamino)methyl]phenol
(13) 3,5-di-tert-butyl-2-[(2-hydroxyethylamino)methyl]phenol
(14) tert-butyl N-(2,4-di-tert-butyl-6-hydroxybenzyl)-beta-alaninate
(15) 3,5-di-tert-butyl-2-[(2-dimethylaminoethylamino)methyl]phenol
(16) 3,5-di-tert-butyl-2-[(3-phenylpropylamino)methyl]phenol
(17) 3,5-di-tert-butyl-2-[(2-phenylethylamino)methyl]phenol
(18) 3,5-di-tert-butyl-2-[(allylamino)methyl]phenol
(19) 5-tert-butyl-2-[(ethylamino)methyl]phenol
(20) 2-[(benzylamino)methyl]-5-tert-butylphenol
(21) 5-tert-butyl-2-[(cyclohexylamino)methyl]phenol
(22) 2-[(cyclohexylamino)methyl]-5-(trichlorovinyl)phenol
(23) 5-tert-butyl-2-{[(2-phenylethyl)amino]methyl}phenol
(24) 2-[(benzylamino)methyl]-5-(trichlorovinyl)phenol
(25) 3,5-di-tert-butyl-2-[(decylamino)methyl]phenol
(26) 2-[(propylamino)methyl]-5-(trichlorovinyl)phenol
(27) 5-tert-butyl-2-[(propylamino)methyl]phenol
(28) 5-tert-butyl-2-[(cyclopropylamino)methyl]phenol
(29) 5-tert-butyl-2-[(1,2,3,4-tetrahydronaphthalen-1-ylamino)methyl]phenol
(30) 2-[(cyclopropylamino)methyl]-5-(trichlorovinyl)phenol
(31) 2-[(isopropylamino)methyl]-5-(trichlorovinyl)phenol
(32) 2-[(1,2,3,4-tetrahydronaphthalen-1-ylamino)methyl]-5-(trichlorovinyl)phenol
(33) 2-[(2,3-dihydro-1H-inden-1-ylamino)methyl]-5-(trichlorovinyl)phenol
(34) 3,5-di-tert-butyl-2-({[(1R)-1-phenylethyl]amino}methyl)phenol
(35) 3,5-di-tert-butyl-2-{[(1-naphthylmethyl)amino]methyl}phenol
(36) 3,5-di-tert-butyl-2-{[(2-naphthylmethyl)amino]methyl}phenol
(37) 2-[(tert-butylamino)methyl]-5-(trichlorovinyl)phenol
(38) 3,5-di-tert-butyl-2-[(1,2,3,4-tetrahydronaphthalen-2-ylamino)methyl]phenol
(39) 2-[(cyclohexylamino)methyl]-3-(trichlorovinyl)phenol
(40) 3,5-di-tert-butyl-2-[(2,3-dihydro-1H-inden-2-ylamino)methyl]phenol
(41) 3,5-di-tert-butyl-2-{[(1R)-2,3-dihydro-1H-inden-1-ylamino]methyl}phenol
(42) 3,5-di-tert-butyl-2-{[(1S)-2,3-dihydro-1H-inden-1-ylamino]methyl}phenol
(43) 5-tert-butyl-2-[(2,3-dihydro-1H-inden-2-ylamino)methyl]phenol
(44) 5-tert-butyl-2-{[(4-methoxybenzyl)amino]methyl}phenol
(45) 5-tert-butyl-2-[(neopentylamino)methyl]phenol
(46) 5-tert-butyl-2-{[(3,3-dimethylbutyl)amino]methyl}phenol
(47) 5-tert-butyl-2-[2-(cyclohexylamino)ethyl]phenol
(48) 5-tert-butyl-2-[(2,3-dihydro-1H-inden-1-ylamino)methyl]phenol
(49) 5-tert-butyl-2-[(isopropylamino)methyl]phenol
(50) 3,5-di-tert-butyl-2-[(decahydronaphthalen-2-ylamino)methyl]phenol
(51) 5-tert-butyl-2-[(isopentylamino)methyl]phenol
(52) 5-tert-butyl-2-[(isobutylamino)methyl]phenol
(53) 5-tert-butyl-2-(piperidin-1-ylmethyl)phenol
(54) 3,5-di-tert-butyl-2-{[(2-pyridin-2-ylethyl)amino]methyl}phenol
(55) 3,5-di-tert-butyl-2-{[(2-pyridin-3-ylethyl)amino]methyl}phenol
(56) 3,5-di-tert-butyl-2-{[(2-pyridin-4-ylethyl)amino]methyl}phenol
(57) 3,5-di-tert-butyl-2-[(tetrahydro-2H-pyran-4-ylamino)methyl]phenol
(58) 3,5-di-tert-butyl-2-{[(cyclohexylmethyl)amino]methyl}phenol
(59) 2-(aminomethyl)-3,5-di-tert-butylphenol
(60) 5-tert-butyl-2-{[(3-methoxybenzyl)amino]methyl}phenol
(61) 2-(aminomethyl)-4-bromo-5-tert-butylphenol
(62) ethyl N-(2,4-ditert-butyl-6-hydroxybenzyl)-beta-alaninate
(63) 3-tert-butyl-2-(piperidin-1-ylmethyl)phenol
(64) 3-tert-butyl-2-[(cyclohexylamino)methyl]phenol
(65) 2-[2-(cyclohexylamino)ethyl]-5-(trichlorovinyl)phenol
(66) 3-tert-butyl-2-[2-(cyclohexylamino)ethyl]phenol
(67) 3,5-di-tert-butyl-2-{[(tetrahydro-2H-pyran-2-ylmethyl)amino]methyl}phenol
(68) 3,5-di-tert-butyl-2-[2-(cyclohexylamino)ethyl]phenol
(69) 3,5-di-tert-butyl-2-{[(3-furylmethyl)amino]methyl}phenol
(70) 2-[2-(benzylamino)ethyl]-3,5-ditert-butylphenol
(71) 2-(Aminomethyl)-3-tert-butyl-5-methylphenol,
(72) 3-(Aminomethyl)-4,6-di-tert-butyl-4'-chlorobiphenyl-2-ol,
(73) 4,6-Di-tert-butyl-3-[(tert-butylamino)methyl]-4'-chlorobiphenyl-2-ol,
(74) 4,6-di-Tert-butyl-3-[(butylamino)methyl]-4'-chlorobiphenyl-2-ol,
(75) 4,6-Di-tert-butyl-4'-chloro-3-[(dimethylamino)methyl]biphenyl-2-ol,
(76) 4,6-Di-tert-butyl-4'-chloro-3-[(diethylamino)methyl]biphenyl-2-ol,
5-Tert-butyl-2-[2-(dimethylamino)ethyl]phenol,
(78) 5-Tert-butyl-2-[2-(methylamino)ethyl]phenol,
(79) 2-(2-Aminoethyl)-3,5-di-tert-butylphenol,
(80) 2-(Aminomethyl)-5-tert-butyl-3-methylphenol,
(81) 2-(Aminomethyl)-3,5-bis(trichlorovinyl)phenol,
(82) 2-(Aminomethyl)-5-(trichlorovinyl)phenol,
(83) 3,5-Di-tert-butyl-2-{[(1,4-dioxan-2-ylmethyl)amino]methyl}phenol,
(84) 3,5-di-tert-butyl-2-({[(1,1-dioxidotetrahydro-3-thienyl)methyl]amino}methyl)phenol,
(85) 5-{[(2,4-di-tert-butyl-6-hydroxybenzyl)amino]methyl}-2,4-dihydro-3H-1,2,4-triazol-3-one,
(86) 2-(1-Aminoethyl)-3,5-di-tert-butylphenol,
(87) 3,5-Di-tert-butyl-2-[1-(ethylamino)ethyl]phenol,
(88) 3,5-Di-tert-butyl-2-[(propylamino)methyl]phenol,
(89) 3,5-Di-tert-butyl-2-{[(pyrazin-2-ylmethyll)amino]methyl}phenol,
(90) 2-(aminomethyl)-3,5-di-tert-butylphenol hydrochloride,
(91) 2-Aminomethyl-5-tert-butylphenol hydrochloride, and pharmaceutically acceptable salts thereof.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119-1190).

When any variable (e.g. aryl, heterocycle, $R^{1a}$, $R^2$ etc.) occurs more than one time in any constituent, its definition on each occurrence is independent at every other occurrence. Also, combinations of substituents/or variables are permissible only if such combinations result in stable compounds.

The term "alkyl" refers to a monovalent alkane (hydrocarbon) derived radical containing from 1 to 15 carbon atoms unless otherwise defined. It may be straight or branched. Preferred alkyl groups include lower alkyls which have from 1 to 6 carbon atoms such as methyl, ethyl, propyl, isopropyl, butyl and t-butyl. When substituted, alkyl groups may be substituted with up to 3 substituent groups, selected from the groups as herein defined, at any available point of attachment. When the alkyl group is said to be substituted with an alkyl group, this is used interchangeably with "branched alkyl group".

Cycloalkyl is a species of alkyl containing from 3 to 15 carbon atoms, without alternating or resonating double bonds between carbon atoms. It may contain from 1 to 4 rings which are fused. Preferred cycloalkyl groups are cyclopropyl, cyclobutyl, cyclopentyl and cyclohexyl. When substituted, cycloalkyl groups may be substituted with up to 3 substituents which are defined herein by the definition of alkyl.

The term "alkoxy" refers to those hydrocarbon groups having an oxygen bridge and being in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

"Halogen" or "halo" as used herein means fluoro, chloro, bromo and iodo.

The term "alkenyl" refers to a hydrocarbon radical straight, branched or cyclic containing from 2 to 11 carbon atoms and at least one carbon to carbon double bond. Preferred alkenyl groups include ethenyl, propenyl, butenyl and cyclohexenyl. Preferably, alkenyl is $C_2$-$C_6$ alkenyl.

Preferably, alkynyl is $C_2$-$C_6$ alkynyl.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

Preferably, heterocycle is selected from 2-azepinonyl, benzimidazolyl, 2-diazapinonyl, imidazolyl, 2-imidazolidinonyl, indolyl, isoquinolinyl, morpholinyl, piperidyl, piperazinyl, pyridyl, pyrrolidinyl, 2-piperidinonyl, 2-pyrimidinonyl, 2-pyrollidinonyl, quinolinyl, tetrahydrofuryl, tetrahydroisoquinolinyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzoyl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, thienyl and triazolyl.

As used herein, unless otherwise specifically defined, substituted alkyl, substituted cycloalkyl, substituted aroyl, substituted aryl, substituted heteroaroyl, substituted heteroaryl, substituted arylsulfonyl, substituted heteroaryl-sulfonyl and substituted heterocycle include moieties containing from 1 to 3 substituents in addition to the point of attachment to the rest of the compound. Preferably, such substituents are selected from the group which includes but is not limited to F, Cl, Br, $CF_3$, $NH_2$, $N(C_1$-$C_6$ alkyl$)_2$, $NO_2$, CN, $(C_1$-$C_6$ alkyl)O—, (aryl)O—, —OH, $(C_1$-$C_6$ alkyl)S(O)$_m$—, $(C_1$-$C_6$ alkyl)C(O)NH—, $H_2$N—C(NH)—, $(C_1$-$C_6$ alkyl)C(O)—, $(C_1$-$C_6$ alkyl)OC(O)—, $(C_1$-$C_6$ alkyl)OC(O)NH—, phenyl, pyridyl, imidazolyl, oxazolyl, isoxazolyl, thiazolyl, thienyl, furyl, isothiazolyl and $C_1$-$C_{20}$ alkyl.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

For use in medicine, the salts of the aminoalkylphenols of formula I will be pharmaceutically acceptable salts. Other salts may, however, be useful in the preparation of the compounds according to the invention or of their pharmaceutically acceptable salts. When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

As used herein, the term "composition" is intended to encompass a product comprising the specified ingredients in the specific amounts, as well as any product which results, directly or indirectly, from combination of the specific ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol Sweetening agents such as those set forth above, and flavoring agents may be added to provide a palatable oral preparation. These compositions may be preserved by the addition of an anti-oxidant such as butylated hydroxyanisole or alphatocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for malaria. Administration occurs in an amount between about 0.1 mg/kg of body weight to about 60 mg/kg of body weight per day, preferably of between 0.5 mg/kg of body weight to about 40 mg/kg of body weight per day.

It is also within the scope of this invention to combine the compounds of this invention with one or more known antimalarial agents such as Chloroquine, Fansidar, Amodiaquine, Quinine, Hialofantrine, Mefloquine, Artemether/Artesunate and Malarone.

Compositions containing the active ingredients of this invention as well as a method for making some of the compounds of formula I are found in U.S. Pat. No. 3,794,734, issued Feb. 26, 1974 and incorporated by reference herein.

The following examples are illustrative of how to prepare various other novel active ingredients of this invention. However, said examples are merely illustrative and should not be construed as limiting the scope of the invention. All substituents are as defined above unless indicated otherwise.

A preferred synthesis of the novel compounds of this invention is shown in reaction Scheme 1 when it is desired that the nitrogen atom of the amino-substituted sidechain be separated from the phenol ring by one carbon atom (n=1 in general formula I). This process involves a Tcherniac-Einhorn amidoalkylation reaction of the phenol of general formula 1 with an N-alkoxymethylamide of general formula 2. The amidoalkylation reaction is generally conducted under acidic reaction conditions which promote the ionization of the alpha-alkoxy group from the amide and produces an acyliminium ion. Acyliminium ions are electrophilic species capable of effecting an electrophilic aromatic substitution reaction of the phenol of general formula 1 and the amidoalkylated phenol of general formula 3 is the product. As stated above, the reaction is conducted under acidic conditions. For instance, the reaction of the phenol of general formula 1 and the amide of general formula 2 may be conducted in solution of an organic acid such as acetic acid. The reaction is promoted by addition of a strong mineral acid such as hydrochloric or sulfuric acid. The reaction may be conducted at a variety of temperatures which depend on the relative reactivity of the phenol (1) and the amide (2) that are selected. Typically the reaction is conducted at ambient temperature for periods of a few hours to a few days. Alternatively, the acidic solvent chosen for the reaction can be a stronger acid such as trifluoracetic acid. In this case it is often not necessary to add a mineral acid to promote the amidoalkylation reaction. Here again, while the optimal reaction temperatures and times will depend on the choices of the phenol (1) and the amide (2) that are selected, frequently these reactions are conducted at ambient temperature for a period of a few hours to a few days.

As shown in reaction Scheme 1, the next step in the synthesis of the novel compounds of general formula I is the hydrolysis of the amide from the intermediate of general formula 3. This hydrolysis reaction is generally conducted in acidic conditions at elevated temperatures. For instance, the amide 3 generally undergoes complete hydrolysis when heated in the presence of a mineral acid such as aqueous hydrochloric or sulfuric acid. The reaction is generally conducted at temperatures between ambient temperature and 100° C. for periods of a few hours to one day, and a co-solvent such as an alcohol is usually added to the reaction mixture. As can be seen in reaction Scheme 1, the substituent labeled X is not incorporated into the product of general formula I. However the hydrolysis of the intermediate of general formula 3 may be accelerated when the group X is a halogen atom. Thus it is preferred to utilize the reagent of general formula 2 with X equal to a halogen atom in the first step of the sequence when it is convenient to do so.

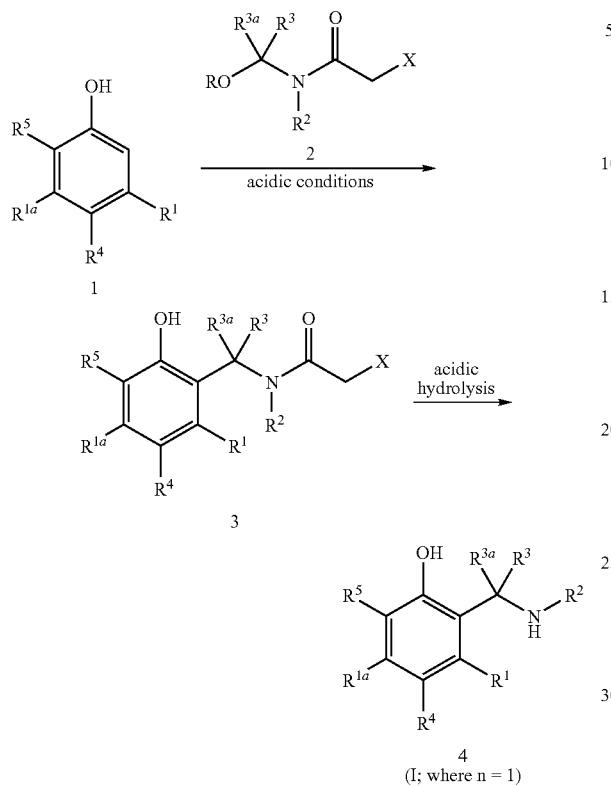

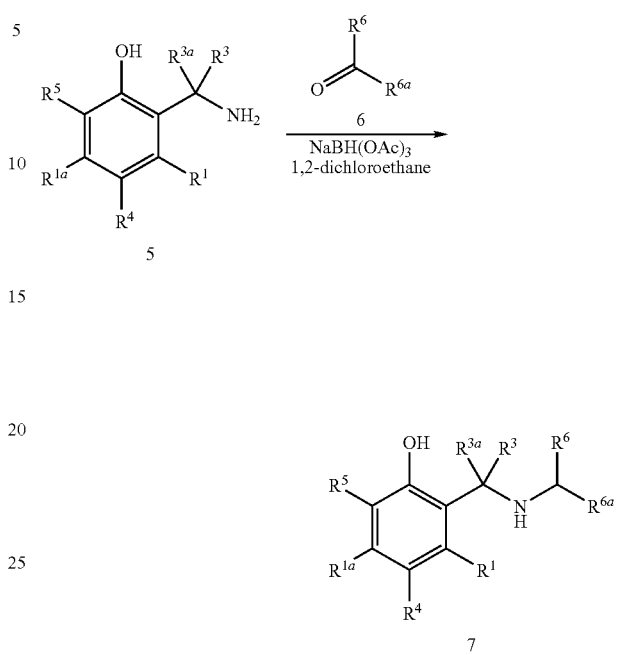

Reaction Scheme 2 illustrates one method for introducing additional substituents onto the amine-containing sidechain of compounds of general formula I. In this case a compound of general formula 5 (I; wherein $R^2$ are both hydrogen) is subjected to reductive amination with an aldehyde or ketone of general formula 6. The reductive amination may be conducted by one of the many methods for this transformation that are known in organic synthesis. For instance, the amine of general formula 5 and the carbonyl compound of general formula 6 are reacted under conditions which promote the formation of an imine, which is then reduced to afford the product of general formula 7 using a reducing agent such as sodium cyanoborohydride or sodium triacetoxyborohydride. A variety of solvents may be employed for this reaction. For instance, when sodium cyanoborohydride is used as the reducing agent, methanol is a frequently used as solvent. Alternatively, when sodium triacetoxyborohydride is the chosen reducing agent, then aprotic solvents such as dichloromethane, 1,2-dichloroethane or toluene are generally used. It is occasionally advantageous to conduct the reaction in two stages. Often, the amine of general formula 5 and the carbonyl compound of general formula 6 are initially induced to form an imine intermediate. The progress of this step may be monitored spectroscopically or chromatographically (e.g. by TLC). Upon completion of imine formation, the reducing agent is then added and the reduction of the imine proceeds to produce the product of general formula 7.

Reaction Scheme 3 illustrates an alternative method for introducing additional substituents onto the amine-containing sidechain of compounds of general formula I. In this case, an amine of general formula 8 (I; wherein $R^2$, $R^3$ and $R^{3a}$ are all hydrogen) is first oxidized using a modification of the Sommelet reaction to afford a substituted salicylaldehyde derivative of general formula 9. The salicylaldehyde 9 is then subjected to reductive amination with a primary or secondary amine of general formula 10 to afford compounds of general formula 11 (I; where $R^3$ and $R^{3a}$ equal hydrogen). The oxidation step is accomplished by heating the amine of general formula 8 with hexamethylenetetramine in an aqueous acidic solvent such as a mixture of water and acetic acid. The reaction is conducted at elevated temperatures, for instance between 100-150° C. for a period of several hours. The reductive amination of the aldehyde of general formula 9 with an amine of general formula 10 is conducted in a manner similar to the reductive amination described for compounds of general formula 5 and 6 in reaction Scheme 2. Typically compounds 9 and 10 are reacted together under conditions that promote formation of an imine and then a reducing agent such as sodium triacetoxyborohydride is added to effect reduction of the imine and formation of the compound of general formula 11. Finally, it is recognized that alternative synthetic methodologies known in organic synthesis may offer advantages for the preparation of the intermediate salicylaldehyde of general formula 9. For instance, depending upon the selection of the other substituents in the final product of general formula I, it may be advantageous to prepare the aldehyde of general formula 9 from a phenol of general formula 1 using a Reimer-Tiemann reaction or a Duff reaction.

Scheme 3

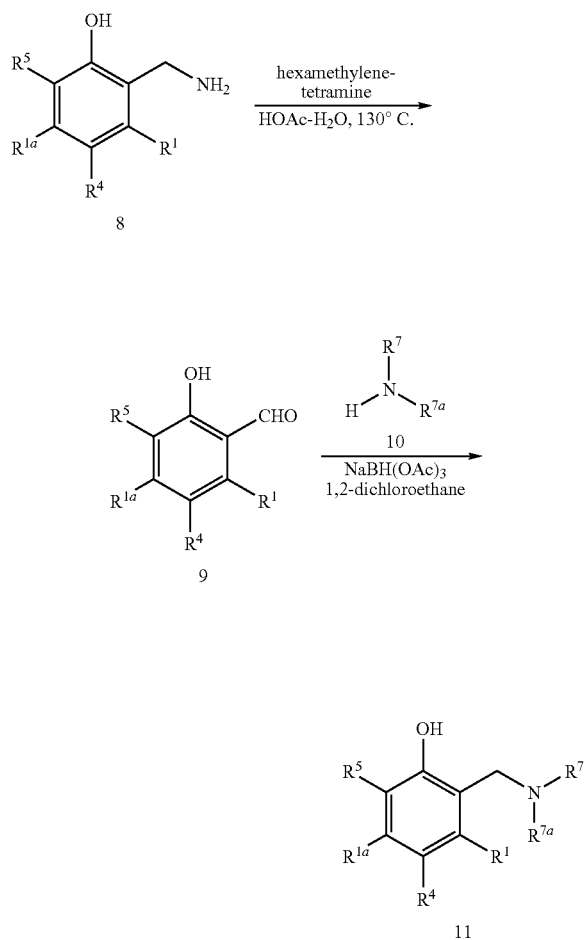

Scheme 4

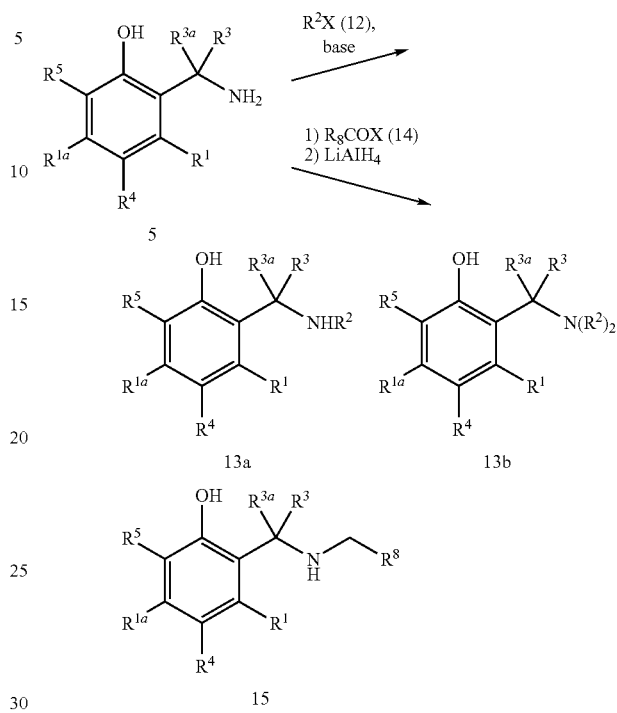

The following examples are illustrative of how to prepare various other novel active ingredients of this invention. However, said examples are merely illustrative and should not be construed as limiting the scope of the invention.

General Procedures.

The HPLC/MS analyses were preformed using a Micromass ZMD mass spectrometer coupled to an Agilent 1100 Series HPLC utilizing a YMC ODS-A 4.6×50 mm column eluting at 2.5 mL/min with a solvent gradient of 10 to 95% B:A over 4.5 min, then 0.5 min at 95% B: solvent A=0.06% TFA in water; solvent B=0.05% TFA in acetonitrile.

Proton NMR spectra were obtained with a 400 MHz Varian Spectrometer in $CDCl_3$ or $CD_3OD$ and chemical shifts are reported as δ using the deuterium of the solvent as standard and coupling constants are reported in hertz.

Reaction Scheme 4 illustrates two additional synthetic methods for the modification of the amine-containing sidechains of the novel compounds of the present invention. In the first reaction, an amine of general formula 5 is reacted with an alkylating agent of formula 12 containing the $R^2$ substituent. In compounds of general formula 12, the group X is a leaving group such as a halogen, mesylate, triflate or the like. The reaction is conducted in a suitable organic solvent such as an alcohol, a halocarbon solvent etc., and the stoichiometry of the reagent 12 is controlled to afford either the mono- or bis-alkylated derivatives 13a or 13b respectively. The reaction at the bottom of reaction Scheme 4 illustrates a two-step conversion of the compound of general formula 5 to a compound of general formula 15. In the first step, the amine of general formula 5 is acylated with an acylating agent of general formula 14. The acylating agent 14 may be either a carboxylic acid halide or anhydride, a mixed-anhydride, or any activated ester typically used to effect the acylation reaction of an amine. In the second step of this sequence, the amide produced in the acylation step is reduced with a reagent capable of reducing amides to amines. For instance, reduction of the intermediate amide with lithium aluminum hydride or diborane in solvents such as TMF produces the amine derivative of general formula 15.

EXAMPLE 1

2-Aminomethyl-5-tert-butylphenol hydrochloride

Step A:
N-(4-tert-butyl-2-hydroxybenzyl)-2-chloroacetamide

A finely powdered mixture of 15 g (0.10 mol) of 3-tert-butylphenol and 12.4 g (0.10 mol) of N-hydroxymethyl-2-chloroacetamide was added in portions to a vigorously stirred solution of 90 mL acetic acid and 10 mL (98%) sulfuric acid at 0° C. The reaction mixture was allowed to warm to room temperature over several hours, and stirring was maintained for a total of 20 hours. The reaction mixture was poured into ice-water, neutralized with saturated aqueous $NaHCO_3$ solution and extracted into $CH_2Cl_2$. The organic extracts were combined, washed with brine, dried ($Na_2SO_4$), filtered and evaporated. The residue was purified on a silica gel flash chromatography column eluted with 10-30% EtOAc in hexane. Evaporation of the purified fractions and drying in vacuo afforded the title compound.

Step B: 2-Aminomethyl-5-tert-butylphenol hydrochloride

To a solution of 50 mL ethanol and 15 mL conc. hydrochloric acid was added 3.58 g (0.014 mol) of the product of Step A and the reaction mixture was stirred and heated to 85° C. using an external oil bath for 3 h. The reaction mixture was then cooled to room temperature and evaporated in vacuo. Excess water was removed from the product mixture by azeotropic distillation of added portions of toluene on a rotary evaporator. The residue was triturated with ether and dried overnight in vacuo to afford the title compound as a white crystalline solid.

HPLC/MS: 162.7 [(M+1)-NH$_3$)]; R$_t$=1.55 min.

EXAMPLE 2

5-tert-Butyl-2-[(ethylamino)methyl]phenol

To a solution of 0.10 g (0.39 mmol) of the product of Step A in Example 1 in 2 mL of anhydrous THF was added 1.95 mL (1.95 mmol) of a 1.0 M solution of lithium aluminum hydride in THF and the reaction mixture was stirred at room temperature for 30 min. The reaction mixture was cooled to room temperature and cautiously quenched with 10% aqueous citric acid. The resulting emulsion was repeatedly extracted with EtOAc and CH$_2$Cl$_2$. The combined organic layers were dried (Na$_2$SO$_4$), filtered and evaporated. The residue was purified on preparative thin-layer chromatography plates eluted with CH$_2$Cl$_2$-MeOH—NH$_4$OH (95:4:1) to afford the title compound.

HPLC/MS: 208.1 (M+1); R$_t$=1.8 min.

EXAMPLE 3

2-[(Benzylamino)methyl]-5-tert-butylphenol

To a mixture of 0.216 g (1.0 mmol) of the product of Example 1 and 0.108 g (0.1 mmol) of benzaldehyde suspended in 5 mL of 1,2-dichloroethane was added 0.5 mL acetic acid and 1 g of finely powdered 4 Å molecular sieves. The reaction mixture was stirred under a nitrogen atmosphere at room temperature overnight, then 1.12 g (5 mmol) of sodium triacetoxyborohydride was added. The reaction was then stirred an addition day at room temperature, then diluted with CH$_2$Cl$_2$ and MeOH. The mixture was filtered through a pad of Celite filter aid eluted with CH$_2$Cl$_2$, and the filtrate was washed with saturated aq. NaHCO$_3$. The organic layer was the separated, dried (Na$_2$SO$_4$), filtered and evaporated in vacuo. The residue was purified on a flash chromatography column eluted with CH$_2$Cl$_2$-MeOH—NH$_4$HO (97:2:1) to afford the title compound.

HPLC/MS: 270.1 (M+1); R$_t$=2.2 min.

EXAMPLES 4-7

Using the procedure described in Example 3 above, reductive amination of the product of Example 1 with the appropriate aldehyde or ketone afforded the following compounds:

| Ex. # | Compound | HPLC-MS m/z (M + 1); R$_t$ (min) |
|---|---|---|
| 4 | 5-tert-Butyl-2-[(cyclohexylamino)methyl]phenol | 262.1; 2.2 |
| 5 | 5-tert-Butyl-2-{[(2-phenylethyl)amino]methyl}phenol | 284.0; 2.5 |
| 6 | 5-tert-Butyl-2-[(2,3-dihydro-1H-inden-2-ylamino)methyl]phenol | 296.1; 2.5 |
| 7 | 5-tert-Butyl-2-{[(3-methoxybenzyl)amino]methyl}phenol | 300.1; 2.4 |

EXAMPLE 8

5-tert-Butyl-2-[(propylamino)methyl]phenol

Step A: 4-tert-Butyl-2-hydroxybenzaldehyde

To a solution of 1.5 g (6.9 mmol) of the product of Example 1 in 15 mL of HOAc-H$_2$O (11:3) was added 1.17 g (8.3 mmol) of hexamethylenetetramine dissolved in 3 mL water. The reaction mixture was magnetically stirred and heated at 130° C. for 3 h at which point 13.5 mL of a 2:1 solution of conc. hydrochloric acid and water was added. The reaction mixture was heated for an additional 10 min at 130° C., then cooled to room temperature and the acetic acid was removed on a rotary evaporator. The residue was partitioned between EtOAc and water, then extracted and the organic layers were combined and dried (Na$_2$SO$_4$). The filtrate was passed through a layer of Celite filter aid mixed with silica gel to remove polar impurities, then evaporated. The residual oil was dried in vacuo and subsequently used in the next step without further purification.

Step B: 5-tert-Butyl-2-[(propylamino)methyl]phenol

To a mixture of 0.178 g (0.1 mmol) of the product of Step A and 0.206 g (3.5 mmol) of n-propylamine dissolved in 10 mL of CH$_2$Cl$_2$ was added 0.5 g of finely powdered 4 Å molecular sieves. The reaction mixture was stirred under a nitrogen atmosphere at room temperature overnight, then 0.53 g (2.5 mmol) of sodium triacetoxyborohydride was added. The reaction was then stirred an addition 8 h at room temperature, then diluted with CH$_2$Cl$_2$ and MeOH. The mixture was filtered through a pad of Celite filter aid eluted with CH$_2$Cl$_2$, and the filtrate was washed with saturated aqueous NaHCO$_3$. The organic layer was the separated, dried (Na$_2$SO$_4$), filtered and evaporated in vacuo. The residue was purified on a flash chromatography column eluted with CH$_2$Cl$_2$-MeOH—NH$_4$OH (95:4:1) to afford the title compound.

HPLC/MS: 222.0 (M+1); R$_t$ 1.9 min.

EXAMPLE 9-18

Using the procedure described in Step B of Example 8 above, reductive amination of the aldehyde produced in Step A from Example 8 with the appropriate amine afforded the following compounds:

| Ex. # | Compound | HPLC-MS m/z (M + 1); $R_t$ (min) |
|---|---|---|
| 9 | 5-tert-Butyl-2-[(cyclopropylamino)methyl]phenol | 220.1; 1.8 |
| 10 | 5-tert-Butyl-2-[(1,2,3,4-tetrahydronaphthalen-1-ylamino)methyl]phenol | 310.1; 2.6 |
| 11 | 5-tert-Butyl-2-{[(4-methoxybenzyl)amino]methyl}phenol | 300.1; 2.5 |
| 12 | 5-tert-Butyl-2-[(neopentylamino)methyl]phenol | 250.2; 2.2 |
| 13 | 5-tert-Butyl-2-{[(3,3-dimethylbutyl)amino]methyl}phenol | 264.1; 2.6 |
| 14 | 5-tert-Butyl-2-[(2,3-dihydro-1H-inden-1-ylamino)methyl]phenol | 296.1; 2.5 |
| 15 | 5-tert-Butyl-2-[(isopropylamino)methyl]phenol | 222.1; 1.9 |
| 16 | 5-tert-Butyl-2-[(isopentylamino)methyl]phenol | 250.1; 2.4 |
| 17 | 5-tert-Butyl-2-[(isobutylamino)methyl]phenol | 236.1; 2.2 |
| 18 | 5-tert-Butyl-2-(piperidin-1-ylmethyl)phenol | 248.2; 2.1 |

EXAMPLE 19

2-(aminomethyl)-3,5-di-tert-butylphenol hydrochloride

Step A: 2-Chloro-N-(2,4-di-tert-butyl-6-hydroxybenzyl)acetamide

A finely powdered mixture of 5.2 g (25 mmol) of 3,5-di-tert-butylphenol and 3.15 g (25 mmol) of N-hydroxymethyl-2-chloroacetamide was added in portions to a vigorously stirred solution of 22.5 mL acetic acid and 2.5 mL (98%) sulfuric acid at 0-10° C. The reaction mixture was allowed to warm to room temperature over several hours, and stirring was maintained for a total of 16 hours. The reaction mixture was poured into ice-water, neutralized with saturated aqueous $NaHCO_3$ solution and extracted into $CH_2Cl_2$. The organic extracts were combined, washed with brine, dried ($Na_2SO_4$), filtered and evaporated. The residue was purified on a silica gel flash chromatography column eluted with 15-30-50% EtOAc in hexane. Evaporation of the purified fractions and drying in vacuo afforded the title compound.

Step B: 2-(Aminomethyl)-3,5-di-tert-butylphenol hydrochloride

To a solution of 50 mL ethanol and 15 mL conc. hydrochloric acid was added 4.35 g (0.014 mol) of the product of Step A and the reaction mixture was stirred and heated to 85° C. using an external oil bath for 3 h. The reaction mixture was then cooled to room temperature and evaporated in vacuo. Excess water was removed from the product mixture by azeotropic distillation of added portions of toluene on a rotary evaporator. The residue was triturated with ether and dried overnight in vacuo to afford the title compound as a white crystalline solid.

HPLC/MS: 218.9 [(M+1)-$NH_3$]; $R_t$=2.3 min.

EXAMPLE 20

3,5-Di-tert-butyl-2-[(ethylamino)methyl]phenol

To 0.311 g (1.00 mmol) of the product of Step A in Example 19 dissolved in 10 mL of THF was added 0.2 g (5.27 mmol) lithium aluminum hydride in portions. The resulting mixture was stirred at room temperature overnight at which point 3 mL of EtOAc was slowly added to decompose the remaining hydride reagent. After stirring an additional 30 min the reaction mixture was quenched by cautious addition of 10% aq. $NH_4Cl$. The resulting mixture was filtered through Celite filter aid, then concentrated in vacuo. The residue was purified on a silica gel flash chromatography column eluted with $CH_2Cl_2$-MeOH—$NH_4OH$ (97:3:0.3) to afford the title compound.

HPLC/MS: 264.2 (M+1); $R_t$=2.69 min.

EXAMPLE 21

3,5-Di-tert-butyl-2-[(butylamino)methyl]phenol

To a mixture of 0.47 g (2.0 mmol) of the product of Example 19 and 0.15 g (2.1 mmol) of n-butyraldehyde in 10 mL of 1,2-dichloroethane was added 25 drops of acetic acid and 3 g of finely powdered 4 Å molecular sieves. The mixture was stirred 5 h at room temperature at which point 1 g of sodium triacetoxyborohydride was added. The reaction mixture was stirred overnight at room temperature, then diluted with 10 mL $CH_2Cl_2$ and filtered through a layer of Celite filter aid. The filtrate was washed with excess saturated aq. $NaHCO_3$, the aqueous layer was extracted with $CH_2Cl_2$, then the organic layers were combined, dried ($Na_2SO_4$), filtered and evaporated. The residue was purified on a silica gel flash chromatography column eluted with 0-10% EtOAc in $CH_2Cl_2$. Evaporation of the purified fractions and drying in vacuo afforded the title compound.

HPLC/MS: 292.2 (M+1); $R_t$=2.8 min.

EXAMPLES 22-34

Using the procedure described in Example 21 above, reductive amination of the product of Example 19 with the appropriate aldehyde or ketone afforded the following compounds;

| Ex. # | Compound | HPLC-MS m/z (M + 1); $R_t$ (min) |
|---|---|---|
| 22 | 3,5-Di-tert-butyl-2-[(cyclohexylamino)methyl]phenol | 318.1; 2.9 |
| 23 | 3,5-Di-tert-butyl-2-[(hexylamino)methyl]phenol | 320,2; 3.2 |
| 24 | 3,5-Di-tert-butyl-2-[(octylamino)methyl]phenol | 348,2; 3.6 |
| 25 | 3,5-Di-tert-butyl-2-[(3-phenylpropylamino)methyl]phenol | 354.1; 3.1 |
| 26 | 3,5-Di-tert-butyl-2-[(2-phenylethylamino)methyl]phenol | 340.1; 3.0 |
| 27 | 3,5-Di-tert-butyl-2-[(decylamino)methyl]phenol | 376.2; 4,1 |
| 28 | 3,5-Di-tert-butyl-2-{[(1-naphthylmethyl)amino]methyl}phenol | 376.1; 3.4 |
| 29 | 3,5-Di-tert-butyl-2-{[(2-naphthylmethyl)amino]methyl}phenol | 376.1; 3.5 |
| 30 | 3,5-Di-tert-butyl-2-[(1,2,3,4-tetrahydronaphthalen-2-ylamino)methyl]phenol | 366.3; 3.2 |

-continued

| Ex. # | Compound | HPLC-MS m/z (M + 1); R$_t$ (min) |
|---|---|---|
| 31 | 3,5-Di-tert-butyl-2-[(decahydronaphthalen-2-ylamino)methyl]phenol | 372.3; 3.6 |
| 32 | 3,5-Di-tert-butyl-2-[(tetrahydro-2H-pyran-4-ylamino)methyl]phenol | 320.2; 2.6 |
| 33 | 3,5-Di-tert-butyl-2-{[(cyclohexylmethyl)amino]methyl}phenol | 332.2; 3.3 |
| 34 | 3,5-Di-tert-butyl-2-{[(3-furylmethyl)amino]methyl}phenol | 316.1; 2.8 |
| 35 | 3,5-Di-tert-butyl-2-{[(pyrazin-2-ylmethyl)amino]methyl}phenol | 328.2; 2.5 |

EXAMPLE 36

3,5-Di-tert-butyl-2-[(methylamino)methyl]phenol

Step A: 2,4-Di-tert-butyl-6-hydroxybenzaldehyde

To a solution of 1.25 g (4.60 mmol) of the product of Example 19 (as the hydrochloride salt) in 10 mL of acetic acid-water (11:3) was added 0.75 g (5.35 mmol) of hexamethylenetetramine. The mixture was refluxed for 3 h then treated with 6 mL of water and 3 mL of conc. hydrochloric acid. Heating was continued for 10 min at which point the reaction mixture was cooled and concentrated in vacuo to remove the acetic acid. The residue was partitioned between EtOAc and water, and the aqueous layer was separated and extracted. The combined organic layers were washed with brine, dried (Na$_2$SO$_4$), filtered and evaporated. The product was purified on a silica gel flash chromatography column eluted with 5% EtOAc-hexane. Evaporation of the purified fractions and drying in vacuo afforded the title compound.

Step B: 3,5-Di-tert-butyl-2-[(methylamino)methyl]phenol

A mixture of 0.234 g (1.00 mmol) of the product of Step A, 3 mL of 2 N methylamine in TMF, and 0.5 mL acetic acid dissolved in 4.0 mL 1,2-dichloroethane was stirred at room temperature for 5 h. Sodium triacetoxyborohydride (0.422 g; 2.0 mmol) and 10 mL of 1,2-dichloroethane was then added and the resulting mixture was stirred overnight at room temperature. The reaction mixture was then treated with excess saturated aqueous NaHCO$_3$. The aqueous layer was separated and extracted with CH$_2$Cl$_2$, the organic layers were combined, dried (Na$_2$SO$_4$), filtered, and evaporated. The residue was purified on a silica gel flash chromatography column eluted with CH$_2$Cl$_2$-MeOH—NH$_4$OH (95:5:0.5). Evaporation of the purified fractions and drying in vacuo afforded the title compound. HPLC/MS: 250.2 (M+1); R$_t$=2.5 min.

EXAMPLES 37-51

Using the procedure described in Step B of Example 35, reductive amination of the aldehyde produced in Step A of Example 35 with the appropriate amine afforded the following compounds:

| Ex. # | Compound | HPLC-MS m/z; R$_t$ (min) |
|---|---|---|
| 37 | 3,5-Di-tert-butyl-2-[(2-hydroxyethylamino)methyl]phenol | 280.2; 2.4 |
| 38 | tert-Butyl N-(2,4-Di-tert-butyl-6-hydroxybenzyl)-beta-alaninate | 364.1; 3.0 |
| 39 | 3,5-Di-tert-butyl-2-[(2-dimethylaminoethylamino)methyl]phenol | 307.1; 2.0 |
| 40 | 3,5-Di-tert-butyl-2-({[(1R)-1-phenylethyl]amino}methyl)phenol | 340.1; 3.1 |
| 41 | 3,5-Di-tert-butyl-2-[(2,3-dihydro-1H-inden-2-ylamino)methyl]phenol | 352.4; 3.1 |
| 42 | 3,5-Di-tert-butyl-2-{[(1R)-2,3-dihydro-1H-inden-1-ylamino]methyl}phenol | 352.2; 3.2 |
| 43 | 3,5-Di-tert-butyl-2-{[(1S)-2,3-dihydro-1H-inden-1-ylamino]methyl}phenol | 352.2; 3.1 |
| 44 | 3,5-Di-tert-butyl-2-{[(2-pyridin-2-ylethyl)amino]methyl}phenol | 341.2; 2.6 |
| 45 | 3,5-Di-tert-butyl-2-{[(2-pyridin-3-ylethyl)amino]methyl}phenol | 341.2; 2.3 |
| 46 | 3,5-Di-tert-butyl-2-{[(2-pyridin-4-ylethyl)amino]methyl}phenol | 341.2; 2.2 |
| 47 | Ethyl N-(2,4-di-tert-butyl-6-hydroxybenzyl)-beta-alaninate | 336.2; 2.9 |
| 48 | 3,5-Di-tert-butyl-2-{[(tetrahydro-2H-pyran-2-ylmethyl)amino]methyl}phenol | 334.2; 3.0 |
| 49 | 3,5-Di-tert-butyl-2-{[(1,4-dioxan-2-ylmethyl)amino]methyl}phenol | 336.2; 2.6 |
| 50 | 3,5-di-tert-butyl-2-({[(1,1-dioxidotetrahydro-3-thienyl)methyl]amino}methyl)phenol | 368.2; 2.5 |
| 51 | 5-{[(2,4-di-tert-butyl-6-hydroxybenzyl)amino]methyl}-2,4-dihydro-3H-1,2,4-triazol-3-one | 333.2; 2.2 |

EXAMPLE 52

2-(1-Aminoethyl)-3,5-di-tert-butylphenol

Step A: N-[1-2,4-di-tert butyl-6-hydroxyphenyl)ethyl]acetamide

To a solution of 2.06 g (10.0 mmol) of 3,5-di-tert-butylphenol in 10 mL of trifluoroacetic acid was added 1.6 g (11.0 mmol) of N-(1-isopropoxyethyl)acetamide and the resulting mixture was stirred overnight at room temperature. The reaction mixture was concentrated in vacuo, and the residue was partitioned between EtOAc and saturated aqueous $NaHCO_3$. The aqueous layers were separated and then extracted with EtOAc. The organic layers were combined, dried ($Na_2SO_4$), filtered and evaporated in vacuo. The product was purified on a silica gel flash chromatography column eluted with 0-25% EtOAc in $CH_2Cl_2$. Evaporation of the purified fraction and drying in vacuo afforded the title compound.
HPLC/MS: 292.1 (M+1); $R_f$=3.3 min.

Step B: 2-(1-Aminoethyl)-3,5-di-tert-butylphenol

Using the hydrolysis procedure described in Step B of Example 19 the product of Step A was converted to the title compound.
HPLC/MS: 233.2 [(M+1)-$NH_3$]; $R_f$=2.67 nm.

EXAMPLE 53

3,5-Di-tert-butyl-2-[1-(ethylamino)ethyl]phenol

Using the procedure described in Example 20, the product of Step A from Example 52 was reduced with lithium aluminum hydride to afford the title compound.
HPLC/MS: 278.4 (M+1); $R_f$=2.91 min.

EXAMPLE 54

3,5-Di-tert-butyl-2-[(propylamino)methyl]phenol

Step A:
3,5-Di-tert-butyl-2-[(propionylamino)methyl]phenyl propionate

To 0.5 g (2.12 mmol) of the product of Example 19 in 20 mL of $CH_2Cl_2$ was added 2 mL triethylamine and 0.5 g (5.4 mmol) of propionyl chloride. The reaction mixture was stirred at room temperature for 1 h then quenched with saturated aq. $NaHCO_3$. The aqueous layer was extracted with $CH_2Cl_2$, the organic layers were combined, dried ($Na_2SO_4$), filtered and evaporated in vacuo. The crude title compound was used directly in the next step without further purification.
HPLC/MS: 275.2 [(M+1)-$NHCOC_2H_5$)]; $R_f$=3.85 min.

Step B:
3,5-Di-tert-butyl-2-[(propylamino)methyl]phenol

Using the procedure described in Example 20, the product of Step A from was reduced with lithium aluminum hydride to afford the title compound.
HPLC/MS: 278.1 (M+1); $R_f$=2.7 min.

EXAMPLE 55

3,5-Di-tert-butyl-2-[(allylamino)methyl]phenol

To 0.705 g (2.99 mmol) of the product of Example 19 in 15 mL of $CH_2Cl_2$ was added 1 g of solid $NaHCO_3$ followed by 0.525 g (3.12 mmol) of allyl iodide. The reaction mixture was stirred overnight at room temperature, then filtered and evaporated in vacuo. The residue was purified on a silica gel flash chromatography column eluted with 0-1% MeOH in $CH_2Cl_2$. Evaporation of the purified fractions and drying in vacuo afforded the title compound.
HPLC/MS: 276.1 (M+1); $R_f$=2.7 min.

EXAMPLE 56

2-(Aminomethyl)-5-(trichlorovinyl)phenol

Step A: 2,2,2-Trichloro-1-(3-methoxyphenyl)ethanol

To a solution of 1.8 mL (22.5 mmol) of chloroform in 10 mL DMF was added 1.4 g (10 mmol) of 3-methoxybenzaldehyde. The reaction mixture was chilled to 0° C. and a solution of 0.40 g (7 mmol) of potassium hydroxide in 1.8 mL of methanol was added. The reaction mixture was stirred for 3 h at 0° C., then quenched by addition of 1 mL of 1 N hydrochloric acid. The reaction mixture was adjusted to pH=7, then extracted with EtOAc. The organic layers were washed with brine, dried ($Na_2SO_4$), filtered and evaporated. The product was used in the next step without further purification.

Step B:
1-Methoxy-3-(1,2,2,2-tetrachloroethyl)benzene

To a suspension of 2.4 g (11.0 mmol) of phosphorous pentachloride in 7.0 mL of $CH_2Cl_2$ was added a solution of 2.28 g (9.0 mmol) of the product of Step A in 5.0 mL of $CH_2Cl_2$. The reaction mixture became homogenous while it was stiffed at room temperature for 3 h. The reaction mixture was then cooled to 0° C. with an external ice-water bath and ice and water were added. The reaction mixture was allowed to warm to room temperature while stirring for 1 h, and was then extracted with $CH_2Cl_2$. The organic layers were combined, dried ($Na_2SO_4$), filtered and evaporated. The residue was purified on a silica gel flash chromatography column eluted with 5-20% EtOAc-hexane. Evaporation of the purified fractions afforded the title compound as a colorless oil.

Step C: 1-Methoxy-3-(trichlorovinyl)benzene

To a magnetically stirred solution of 0.228 g (5.7 mmol) of sodium hydroxide in 2.0 mL methanol was slowly added a solution of 1.2 g (4.4 mmol) of the product of Step B in 1.0 mL methanol. A white precipitate was deposited and the reaction mixture was stirred for an additional 3 h. At this point the reaction mixture was evaporated in vacuo and the residue was purified on a silica gel flash chromatography column eluted with hexane. Evaporation of the purified fractions afforded the title compound.

Step D: 3-(Trichlorovinyl)phenol

A solution of 3.0 g (12.0 mmol) of boron tribromide in 10 mL of $CH_2Cl_2$ was magnetically stirred at 0° C. with an external ice-water bath, while a solution of 2.38 g (10.0 mmol) of the product of Step C in 20 mL $CH_2Cl_2$ was slowly added over a period of 1 h. At this point the reaction mixture was allowed to slowly warm to room temperature and stirring was continued for an additional 5 h. The reaction was again cooled to 0° C. and quenched by addition of 40 mL water. The organic layer was separated and then washed with 2 N NaOH. The aqueous extracts were acidified with 1 N HCl and extracted with ether. The organic extracts were combined, washed with brine, dried (MgSO$_4$), filtered and evaporated in vacuo to afford the title compound which was used directly in the next step without further purification.

Step E: 2-Chloro-N-[2-hydroxy-4-(trichlorovinyl) benzyl]acetamide

A mixture of 2.02 g (9.0 mmol) of the product of Step D and 1.10 g (9.0 mmol) of N-hydroxymethyl-2-chloroacetamide was added in portions to a vigorously stirred solution of 9.0 mL acetic acid and 1.0 mL (98%) sulfuric acid at 0-10° C. The reaction mixture was allowed to warm to room temperature over several hours, and stirring was maintained for a total of 2 days. The reaction mixture was poured into ice-water, neutralized with saturated aqueous NaHCO$_3$ solution and extracted into CH$_2$Cl$_2$. The organic extracts were combined, washed with brine, dried (Na$_2$SO$_4$), filtered and evaporated. The residue was purified on a silica gel flash chromatography column eluted with a gradient of 10-30% EtOAc in hexane. Evaporation of the purified fractions and drying in vacuo afforded the title compound.

Step F: 2-(Aminomethyl)-5-(trichlorovinyl)phenol

To a solution of 5 mL ethanol and 1.5 mL conc. hydrochloric acid was added 0.818 g (2.5 mmol) of the product of Step E and the reaction mixture was stirred and heated to 85° C. using an external oil bath overnight. The reaction mixture was then cooled to room temperature and evaporated in vacuo. The residue was triturated with ether and dried overnight in vacuo to afford the title compound as a white crystalline solid.
HPLC/MS: 236.9 [(M+1)-NH$_3$]; R$_t$ 2.0 min.

EXAMPLE 57

2-[(Ethylamino)methyl]-5-(trichlorovinyl)phenol

Using the procedure described in Example 2, the product of Step E in Example 56 may be reduced with lithium aluminum hydride to afford the title compound.

EXAMPLES 58 and 59

Using the procedure described in Example 3, the product of Step F in Example 56 was subjected to reductive amination with cyclohexanone and benzaldehyde to afford the following compounds respectively:

2-[(Cyclohexylamino)methyl]-5-(trichlorovinyl)phenol which had:
HPLC/MS: 334.0 (M+1); R$_t$=2.5 min.

2-[(Benzylamino)methyl]-5-(trichlorovinyl)phenol which had:
HPLC/MS: 342.0 (M+1); R$_t$=2.5 min.

EXAMPLE 60

2-[(Propylamino)methyl]-5-(trichlorovinyl)phenol

Step A: 2-Hydroxy-4-(trichlorovinyl)benzaldehyde

To a solution of 0.375 g (1.3 mmol) of the product of Step F in Example 56 in 3.0 mL of HOAc-H$_2$O (11:3) was added 1.17 g (8.3 mmol) of hexamethylenetetramine dissolved in 1.0 mL water. The reaction mixture was magnetically stirred and heated at 130° C. for 3 h at which point 3 mL of a 2:1 solution of water and conc. hydrochloric acid was added. The reaction mixture was heated for an additional 10 min at 130° C., then cooled to room temperature and the acetic acid was removed on a rotary evaporator. The residue was partitioned between EtOAC and water, then extracted. The organic layers were combined and dried (Na$_2$SO$_4$). The filtrate was passed through a layer of Celite filter aid, then evaporated. The residual oil was dried in vacuo and subsequently used in the next step without further purification.

Step B:
2-[(Propylamino)methyl]-5-(trichlorovinyl)phenol

To a mixture of 0.211 g (0.84 mmol) of the product of Step A and 0.177 g (2.94 mmol) of n-propylamine dissolved in 8 mL of CH$_2$Cl$_2$ was added 0.5 g of finely powdered 4 Å molecular sieves. The reaction mixture was stirred under a nitrogen atmosphere at room temperature overnight, then 0.445 g (2.1 mmol) of sodium triacetoxyborohydride was added. The reaction was then stirred an addition 8 h at room temperature, then diluted with CH$_2$Cl$_2$ and MeOH. The mixture was filtered through a pad of Celite filter aid eluted with CH$_2$Cl$_2$, and the filtrate was washed with saturated aqueous NaHCO$_3$. The organic layer was the separated, dried (Na$_2$SO$_4$), filtered and evaporated in vacuo. The residue was purified on a silica gel flash chromatography column eluted first with CH$_2$Cl$_2$-MeOH—NH$_4$OH (96:3:1) followed by CH$_2$Cl$_2$-MeOH—NH$_4$OH (94:5:1). Evaporation of the purified fractions and drying in vacuo afforded the title compound.
HPLC/MS: 293.8 (M+1); R$_t$=2.2 min.

EXAMPLES 61-65

Using the procedure described in Step B of Example 8 above, reductive amination of the aldehyde produced in Step A from Example 57 with the appropriate amine afforded the following compounds

| Ex. # | Compound | HPLC-MS m/z (M + 1); R$_t$ (min) |
|---|---|---|
| 61 | 2-[(cyclopropylamino)methyl]-5-(trichlorovinyl)phenol | 291.9; 2.1 |
| 62 | 2-[(isopropylamino)methyl]-5-(trichlorovinyl)phenol | 293.8; 2.1 |
| 63 | 2-[(1,2,3,4-tetrahydronaphthalen-1-ylamino)methyl]-5-(trichlorovinyl)phenol | 382.0; 2.7 |
| 64 | 2-[(2,3-dihydro-1H-inden-1-ylamino)methyl]-5-(trichlorovinyl)phenol | 368.0; 2.6 |
| 65 | 2-[(tert-butylamino)methyl]-5-(trichlorovinyl)phenol | 307.9; 2.2 |

EXAMPLE 66

2-(Aminomethyl)-3,5-bis(trichlorovinyl)phenol

Step A: 1-Methoxy-3,5-bis(1-hydroxy-2,2,2-trichloroethyl)benzene

To a solution of 0.60 g (5 mmol) of chloroform in 2 mL DMF was added 0.1 64 g (1.0 mmol) of 5-methoxy-1,3-diformylbenzene (Provent, C; Chautemps, P.; Gellon, G.; Pierre, J.-L. *Tetrahedron Lett.* 1996, 347 1393-96). The reaction mixture was chilled to 0° C. and a solution of 39.5 mg (0.7 mmol) of potassium hydroxide in 0.2 mL of methanol was added. The reaction mixture was stirred for 20 min at 0°

C., then was quenched by addition of 1 mL of 1 N hydrochloric acid. The reaction mixture was adjusted to pH=7, then extracted with EtOAc. The organic layers were washed with brine, dried (Na$_2$SO$_4$), filtered and evaporated. The product was used in the next step without further purification.

Step B:
1-Methoxy-3,5-bis(1,2,2,2-tetrachloroethyl)benzene

To a suspension of 0.376 g (1.8 mmol) of phosphorous pentachloride in 0.5 mL of CH$_2$Cl$_2$ was added a solution of 0.301 g (0.75 mmol) of the product of Step A in 0.4 mL of CH$_2$Cl$_2$. The reaction mixture became homogenous while it was stirred at room temperature for 30 min. The reaction mixture was then quenched by addition of ice and water, then allowed to warm to room temperature while stirring for 30 min. The reaction mixture was extracted with CH$_2$Cl$_2$, the organic layers were combined, dried (Na$_2$SO$_4$), filtered and evaporated. The residue was purified on a silica gel flash chromatography column eluted with 0-20% EtOAc-hexane. Evaporation of the purified fractions afforded the title compound.

Step C: 1-Methoxy-3,5-bis(trichlorovinyl)benzene

To a magnetically stirred solution of 30 mg (0.73 mmol) of sodium hydroxide in 0.2 mL methanol was slowly added a solution of 0.122 g (0.28 mmol) of the product of Step B in 0.1 mL methanol. A white precipitate was deposited and the reaction mixture was then stirred overnight. The reaction mixture was then evaporated in vacuo and the residue was purified on a silica gel flash chromatography column eluted with hexane. Evaporation of the purified fractions afforded the title compound.

Step D: 3,5-Bis(trichlorovinyl)phenol

A solution of 0.153 g (0.6 mmol) of boron tribromide in 0.5 mL of CH$_2$Cl$_2$ was magnetically stirred at 0° C. with an external ice-water bath, while a solution of 0.093 g (0.25 mmol) of the product of Step C in 0.5 mL CH$_2$Cl$_2$ was added over a period of 5 min. The reaction mixture was stirred an additional 30 min at 0° C. then allowed to warm to room temperature and stirring was continued overnight. The reaction was again cooled to 0° C. and quenched by addition of 1.0 mL water. The organic layer was separated and then washed with 2 N NaOH. The aqueous extracts were acidified with 1 N HCl and extracted with ether. The organic extracts were combined, washed with brine, dried (MgSO$_4$), filtered and evaporated in vacuo. The residue was purified on a silica gel flash chromatography column eluted with 5% EtOAc-hexane. Evaporation of the purified fractions and drying in vacuo afforded the title compound.

Step E: 2-Chloro-N-[2-hydroxy-4,6-bis(trichlorovinyl)benzyl]acetamide

A mixture of 0.352 g (1.0 mmol) of the product of Step D and 0.123 g (1.0 mmol) of N-hydroxymethyl-2-chloroacetamide was added in portions to a vigorously stirred solution of 0.9 mL acetic acid and 0.1 mL (98%) sulfuric acid at 0-10° C. The reaction mixture was allowed to warm to room temperature, and stirring was maintained for a total of 4 days. The reaction mixture was poured into ice-water, neutralized with saturated aqueous NaHCO$_3$ solution and extracted into CH$_2$Cl$_2$. The organic extracts were combined, washed with brine, dried Na$_2$SO$_4$, filtered and evaporated. The residue was purified on a silica gel flash chromatography column eluted with 5-10% EtOAc in hexane. Evaporation of the purified fractions and drying in vacuo afforded the title compound.

Step F:
2-(Aminomethyl)-3,5-bis(trichlorovinyl)phenol

To a solution of 0.2 mL ethanol and 60 μL conc. hydrochloric acid was added 0.025 g (0.05 mmol) of the product of Step E and the reaction mixture was stirred and heated to 85° C. using an external oil bath overnight. The reaction mixture was then cooled to room temperature and evaporated in vacuo. The residue was triturated with ether and dried overnight in vacuo to afford the title compound as a white crystalline solid.

HPLC/MS: 381.9 (M+1), 364.8 [(M+1)-NH$_3$]; R$_t$=2.6 min.

EXAMPLE 67

3,5-Bis(trichlorovinyl)-2-[(ethylamino)methyl]phenol

Using the procedure described in Example 2, the product of Step E in Example 53 was reduced with lithium aluminum hydride to afford the title compound.

HPLC/MS: 409.8 (M+1); R$_t$=2.9 min.

EXAMPLE 68

2-(Aminomethyl)-5-tert-butyl-3-methylphenol

Step A: N-(4-tert-butyl-2-hydroxy-6-methylbenzyl)-2-chloroacetamide and N-(2-tert-butyl-6-hydroxy-4-methylbenzyl)-2-chloroacetamide To a solution of 1.64 g of 3-tert-butyl-5-methylphenol (prepared from commercially available 2-tert-butyl-5-methylphenol according to U.S. Pat. No. 3,880,937) and 1.5 g of N-hydroxymethyl-2-chloroacetamide is added 10 mL of TFA. The reaction mixture was stirred overnight at room temperature, then poured into 200 mL water and neutralized with NaHCO$_3$. The organic layer was separated and the aqueous layer was extracted with three times with 50 mL CH$_2$Cl$_2$. The combined extracts were dried (Na$_2$SO$_4$), filtered and evaporated in vacuo. The residue was purified on a silica gel flash chromatography column eluted with a gradient of 5-50% EtOAc in hexane which afforded three products in the following order of elution: N-(4-tert-butyl-2-hydroxy-6-methylbenzyl)-2-chloroacetamide, N-(2-tert-butyl-6-hydroxy-4-methylbenzyl)-2-chloroacetamide and N,N'-[(4-tert-butyl-2-hydroxy-6-methyl-1,3-phenylene)di(methylene)]bis(2-chloroacetamide).

Step B:
2-(Aminomethyl)-5-tert-butyl-3-methylphenol

To 0.2 g of N-(4-tert-butyl-2-hydroxy-6-methylbenzyl)-2-chloroacetamide from Step A in 10 mL of 95% ethanol was added 1 mL HCl. The resulting mixture was refluxed for 4 h then aged overnight at 50° C. The reaction mixture was concentrated to remove the ethanol and then partitioned between EtOAc and saturated aqueous NaHCO$_3$. The organic layer was dried (Na$_2$SO$_4$), filtered and evaporated to afford the title compound.

HPLC/MS: 177.1 [(M+1)-NH3]; Rt=2.75 min.

EXAMPLE 69

2-(Aminomethyl)-3-tert-butyl-5-methylphenol

Using the procedure described in Step B of Example 68, N-(2-tert-butyl-6-hydroxy-4-methylbenzyl)-2-chloroacetamide from Step A of Example 68 was converted to the title compound.

HPLC/MS: 177.1 [(M+1)-NH$_3$]; R$_t$=2.87 min.

EXAMPLE 70

3-(Aminomethyl)-4,6-di-tert-butyl-4'-chlorobiphenyl-2-ol

Step A: 2,4-Di-tert-butyl-4'-chloro-6-methoxybiphenyl

A solution of 9.0 g (30.1 mmol) of 2-bromo-1,5-di-tert-butyl-3-methoxybenzene (Zhang, H.; Kwong, F. Y.; Tian, Y.; Chan, K. S. *J. Org. Chem.* 1998, 63, 6886-6890) in 100 mL of DME was purged with nitrogen for 15 min and 1.5 g (0.13 mmol) of tetrakis(triphenylphosphine)palladium(0) was added. After stirring 20 min 5.0 g (31.9 mmol) of 4-chlorobenzeneboronic acid was added. The reaction mixture was stirred at 75° C. and 15 mL of 5 N sodium hydroxide was added dropwise. The resulting mixture was then stirred overnight at 80° C. The reaction mixture was then cooled to room temperature and the DME was removed in vacuo. The residue was partitioned between water and hexane containing 10% EtOAc and extracted. The organic layer was dried, filtered and evaporated to afford the title compound suitable for use in the next step.

Step B: 4,6-di-tert-butyl-4'-chlorobiphenyl-2-ol

A solution of 4.9 g (14.8 mmol) of the product of Step A in 30 mL of CH$_2$Cl$_2$ was placed in an external cooling bath containing dry ice and acetone and stirred under a nitrogen atmosphere. A 1.0 M solution of boron tribromide (20 mL, 20.0 mmol) in CH$_2$Cl$_2$ was added dropwise. After the addition was complete, the reaction mixture was stirred an additional 5 min then allowed to warm to room temperature. After stirring 1 h the reaction mixture was poured into 500 mL ice water and was stirred for 30 min. The aqueous layer was separated and extracted with 100 mL CH$_2$Cl$_2$. The organic layers were combined, dried Na$_2$SO$_4$), filtered and evaporated in vacuo. The residue was purified on a silica gel flash chromatography column eluted with 3% EtOAc-hexanes. Evaporation of the purified fractions and drying in vacuo afforded the title compound.

Step C: 2-chloro-N-[(4,6-di-tert-butyl-4'-chloro-2-hydroxybiphenyl-3-yl)methyl]acetamide To a solution of 3.0 g (9.5 mmol) of the product of Step B and 1.25 g (10.1 mmol) of N-hydroxymethyl-2-chloroacetamide in 20 mL CH$_2$Cl$_2$ was added 25 mL of trifluoroacetic acid. The reaction mixture was stirred under a nitrogen atmosphere overnight and then concentrated in vacuo. The residue was partitioned between EtOAc and excess saturated aqueous NaHCO$_3$. The aqueous layer was separated and re-extracted with EtOAc. The organic layers were then combined, dried (Na$_2$SO$_4$), filtered and evaporated in vacuo to afford the title compound.

Step D: 3-(Aminomethyl)-4,6-di-tert-butyl-4'-chlorobiphenyl-2-ol

To a mixture of 0.30 g (0.71 mmol) of the product from Step C in 20 mL ethanol was added 3 mL conc. hydrochloric acid and the resulting solution was stirred and heated overnight at 75° C. The reaction mixture was then cooled to room temperature, concentrated in vacuo and the residue was partitioned between EtOAc and saturated aqueous NaHCO$_3$. The aqueous layer was separated and re-extracted with EtOAc. The organic layers were combined, dried Na$_2$SO$_4$), filtered and evaporated in vacuo to afford the title compound.

HPLC/MS: 329.2 (M+1); R$_t$=3.28 min.

EXAMPLE 71

4,6-Di-tert-butyl-3-[(tert-butylamino)methyl]-4'-chlorobiphenyl-2-ol

Step A: 4,6-Di-tert-butyl-4'-chloro-2-hydroxybiphenyl-3-carbaldehyde

Using the procedure described in Step A of Example 8 above, the product of Step D in Example 70 was converted to the title compound.

Step B: 4,6-Di-tert-butyl-3-[(tert-butylamino)methyl]-4'-chlorobiphenyl-2-ol

Using the procedure described in Step B of Example 8 above, the product of Step A and tert-butylamine were converted to the title compound.

HPLC/MS: 402.1 (M+1); R$_t$=3.6 min.

EXAMPLES 72-74

Using the procedure described in Step B of Example 8 above, the product of Step A in Example 71 and the appropriate amines were converted to the following compounds:

| Ex. # | Compound | HPLC-MS m/z (M + 1); R$_t$ (min) |
|---|---|---|
| 72 | 4,6-di-Tert-butyl-3-[(butylamino)methyl]-4'-chlorobiphenyl-2-ol | 402.1; 3.6 |
| 73 | 4,6-Di-tert-butyl-4'-chloro-3-[(dimethylamino)methyl]biphenyl-2-ol | 374.1; 3.44 |
| 74 | 4,6-Di-tert-butyl-4'-chloro-3-[(diethylamino)methyl]biphenyl-2-ol | 402.1; 3.6 |

EXAMPLE 75

5-Tert-butyl-2-[2-(dimethylamino)ethyl]phenol

Step A: (4-Tert-butyl-2-methoxyphenyl)acetic acid

A mixture of 5.76 g (27.9 mmol) of 1-(4-tert-butyl-2-methoxyphenyl)ethanone (described in patent applications WO 01/02366; WO 99/52857; WO 99/21836; WO 97/48683), 1.1 g (34.3 mmol) sulfur and 15 mL morpholine (0.172 mol) was refluxed overnight under a nitrogen atmosphere. The reaction mixture was cooled and poured into 200 mL water containing 30 g sodium hydroxide and the resulting mixture was again refluxed overnight. The reaction mixture was then cooled to room temperature, diluted with an equal volume of water, and filtered through a pad of Celite filter aid. The filtrate was then cooled with an external ice water bath and acidified. The resulting precipitate was filtered, washed with water and air dried. The residue was then suspended in EtOAc and filtered to remove insoluble material and the filtrate was concentrated in vacuo to afford the title compound.

Step B: (4-Tert-butyl-2-methoxyphenyl)acetyl chloride

To 0.52 g (0.23 mmol) of the product of Step A was added 10 mL $CH_2Cl_2$ and 1 mL triethylamine. The resulting solution was concentrated in vacuo to remove the solvent and excess triethylamine. The residual triethylammonium salt was re-dissolved in 10 mL $CH_2Cl_2$ and 1.0 mL of oxalyl chloride was added. After stirring 30 min the reaction mixture was evaporated in vacuo to afford the title compound which was used in the next step without further purification.

Step C: 2-(4-Tert-butyl-2-methoxyphenyl)-N,N-dimethylacetamide

The product of Step B was dissolved in 20 mL $CH_2Cl_2$ and 5.0 mL of a 2 M solution of dimethylamine in tetrahydrofuran was added. The reaction mixture was stirred overnight at room temperature, and then concentrated in vacuo. The residue was partitioned between 50 mL EtOAc, 20 mL water and 10 mL of 5 N sodium hydroxide. The aqueous layer was separated and re extracted with EtOAc, then the organic layers were combined, dried $Na_2SO_4$), filtered and evaporated in vacuo to afford the title compound.

Step D: [2-(4-Tert-butyl-2-methoxyphenyl)ethyl]dimethylamine

To a solution of 0.323 g (0.13 mmol) of the product of Step C in 10 mL of anhydrous THF was carefully added 0.1 g (2.63 mmol) of lithium aluminum hydride. The reaction mixture was then stirred overnight under a nitrogen atmosphere at 65° C. The reaction mixture was then cooled using an external ice water bath, 5.0 mL EtOAc was added. The reaction mixture was stirred an additional 20 min, at which point an excess of 2.5 N aqueous sodium hydroxide was added, followed by 50 mL EtOAc. The aqueous layer was separated and re-extracted with EtOAc. The organic layers were combined, dried ($Na_2SO_4$), filtered and evaporated in vacuo to afford the title compound.

Step E: 5-Tert-butyl-2-[2-(dimethylamino)ethyl]phenol

A mixture of 0.092 g (0.39 mmol) of the product from step D and 3.0 mL of 48% aqueous hydrobromic acid was refluxed for 1 h. The reaction mixture was cooled to room temperature and partitioned between saturated aqueous $NaHCO_3$ and ether. The aqueous layer was separated and re extracted with ether. The organic layers were combined, dried ($Na_2SO_4$), filtered and evaporated in vacuo to afford the title compound.

HPLC/MS; 222.1 (M+1); Rt=1.9 min.

EXAMPLE 76

5-Tert-butyl-2-[2-(methylamino)ethyl]phenol

Reaction of the product of Step B in Example 75 with methylamine instead of dimethylamine as described in Step C of Example 75 afforded 2-(4-tert-butyl-2-methoxyphenyl)-N-methylacetamide. Treatment of this later product according to the procedures described in Steps D and E of example 75 affords the title compound.

HPLC/MS: 208.2 (M+1); Rt=2.8 min.

EXAMPLE 77

2-(2-Aminoethyl)-3,5-di-tert-butylphenol

Step A: 2-(Benzyloxy)-4,6-di-tert-butylbenzaldehyde

To a solution of 1.17 g (5.0 mmol) of 2,4-di-tert-butyl-6-hydroxybenzaldehyde (from Step A of Example 35) in 10 mL of dry DMF was added 0.25 g (10.4 mmol) of powdered sodium hydride and the resulting mixture was stirred for 30 min under a nitrogen atmosphere. Benzyl bromide (1.0 g, 5.9 mmol) was then added and the resulting mixture was stirred for an additional 3 h. The reaction mixture was then concentrated in vacuo and the residue was partitioned between ether and water. The aqueous layer was re extracted with ether and the organic layers were then combined, dried ($Na_2SO_4$), filtered and evaporated. The residue was purified on a silica gel flash chromatography column eluted with 0-10% EtOAc-hexane. Combination of the purified fractions and drying in vacuo afforded the title compound.

Step B: 1-(Benzyloxy)-3,5-di-tert-butyl-2-[2-nitrovinyl]benzene

To a mixture of 1.5 g (4.6 mmol) of the product of Step A and 2.0 g of ammonium acetate in 25 mL acetic acid was added 3 mL nitromethane. The reaction mixture was refluxed for 5 h, then cooled to room temperature and the volatiles were removed in vacuo. The residue was partitioned between EtOAc and water, then separated. The aqueous layer was re-extracted with EtOAc, the organic layers were combined, dried ($Na_2SO_4$), filtered and evaporated in vacuo. The residue was purified on a silica gel flash chromatography column eluted with 0-20% $CH_2Cl_2$-hexane. Combination of the purified fractions and drying in vacuo afforded the title compound.

Step C: 2-(2-Aminoethyl)-3,5-di-tert-butylphenol

To a solution of 0.183 g (0.5 mmol) of the product of Step B in 10 mL of methanol was added 0.1 g of 10% palladium on carbon catalyst and the reaction mixture was stirred in Parr shaker under 40 psig of hydrogen overnight. The reaction mixture was then filtered through Celite filter aid and the filtrate was evaporated in vacuo. The residue was purified on a silica gel flash chromatography column eluted with mixtures of $CH_2Cl_2$/MeOH/conc. $NH_4OH$ of the following compositions: 97/3/0.3; 95/5/0.5; and 90/10/1. Combination of the purified fractions and drying in vacuo afforded the title compound.

HPLC/MS: 250.1 (M+1); Rt=2.6 min.

EXAMPLE 78

2-[2-(Benzylamino)ethyl]-3,5-di-tert-butylphenol

The product of Example 75 (0.143 g) was treated with 0.060 g (0.58 mmol) of benzaldehyde according to the procedure described in Example 3. The product was purified on a silica gel flash chromatography column eluted with 5% isopropanol in hexane. Evaporation of the purified fractions and drying in vacuo afforded the title compound.

HPLC/MS: 340.1 (M+1); Rt=3.1 min.

EXAMPLE 79

3,5-Di-tert-butyl-2-[2-(cyclohexylamino)ethyl]phenol

Step A: {2-[2-(Benzyloxy)-4,6-di-tert-butylphenyl]ethyl}amine

To a suspension of 0.0 g (4.59 mmol) of lithium borohydride in 3 mL THF was carefully added 1.3 mL (10.2 mmol) of chlorotrimethylsilane. The reaction mixture was stirred for 2 min and then a solution of 0.367 g (1.0 mmol) of 1-(benzyloxy)-3,5-di-tert-butyl-2-[2-nitrovinyl]benzene from Step B of Example 75 dissolved in 1.5 mL of anhydrous THF was slowly added. The resulting reaction mixture was stirred overnight at room temperature then cooled using an external ice water bath and 15 mL of methanol was slowly added. The resulting mixture was evaporated in vacuo, the residue was the treated with 20 mL of 5 N aqueous sodium hydroxide and then the reaction mixture was extracted with 5 times with 20 mL portions of $CH_2Cl_2$. The combined extracts were dried $Na_2SO_4$), filtered and evaporated in vacuo. The residue was purified on a silica gel flash chromatography column eluted initially with 5% MeCOH in $CH_2Cl_2$ followed by a 95/5/0.5 mixture of $CH_2Cl_2$-MeOH-conc. $NH_4OH$. Combination of the purified fractions and evaporation in vacuo afforded the title compound.

Step B: {2-[2-(Benzyloxy)-4,6-di-tert-butylphenyl]ethyl}cyclohexylamine

The product from Step A (0.227 g) was treated with 0.070 g (0.71 mmol) of cyclohexanone according to the procedure described in Example 3. The product was purified on a silica gel flash chromatography column eluted with 5-10% isopropanol in hexane. Evaporation of the purified fractions and drying in vacuo afforded the title compound.

Step C: 3,5-Di-tert-butyl-2-[2-(cyclohexylamino)ethyl]phenol

A solution of 0.125 g (0.30 mmol) of the product of Step B dissolved in 10 mL ethanol was purged with nitrogen for 10 min, then 0.05 g of 10% palladium on carbon catalyst and 1 mL (10.6 mmol) of 1,4-cyclohexadiene was added and the reaction mixture was stirred overnight at room temperature. An additional 0.05 g of 10% palladium on carbon catalyst and 1 mL (10.6 mmol) of 1,4-cyclohexadiene was added and the reaction mixture was then refluxed for 1 h. The reaction mixture was then cooled to room temperature and filtered through a pad of Celite filter aid. The filtrate was concentrated in vacuo and the residue was purified on a silica gel flash chromatography column eluted with 50% EtOAc in hexane. Combination of the purified fractions and drying in vacuo afforded the title compound.

HPLC/MS: 332.3 (M+1); Rt=3.1 min.

*Plasmodium Falciparum* Assay In Vitro (PFAIV)

The PFAIV assay is an in vitro assay designed to identify potential inhibitors of *Plasmodium falciparum* by measuring the incorporation of tritiated hypoxanthine into parasitized red blood cells.

The following method is an adaptation of the method described by Desjardins, R E et al, 1979. AAC Vol 16 p 710-718:

1. Sixty microliters of a solution of RPMI 1640 media plus (1:100 dilution) gentamycin containing desired concentration of test compound is added to the wells of a 96-well plate. (For titrations, 120 microliters is added to the top well and the compounds are serially diluted into 60 microliters of media.)

2. Fifty three microliters of parasitized red blood cells is added to the wells. The parasitemia of the culture is approximately 2-3% and the hematocrit is 5%. The red blood cells are diluted in RPMI1640 media containing 20% human A+serum and gentamycin.

3. Twelve microliters of RPMI1640 media containing 200 µCi (1:25 dilution of 1 µCi/ml solution) is added to each well.

4. The plates are incubated at 37% for 48 hours under reduced $CO_2$ conditions (candle jar). After incubation, the plates are frozen overnight, then thawed and harvested on a manual 96-well harvester onto Unifilter GF/B plates.

5. The plates are counted on a Wallac microbeta and % inhibition of parasite growth is determined as compared to control wells containing no compound.

The compounds of this invention have IC50 of $\leqq$1 ug/ml.

What is claimed is:

1. A pharmaceutical composition for the treatment of malaria, which comprises a compound of formula I:

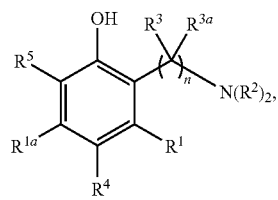

or a pharmaceutically acceptable salt or enantiomer or diastereomer thereof, a second anti-malarial agent, and a pharmaceutically acceptable carrier;
wherein:
$R^5$ is hydrogen;
$R^{1a}$ and $R^1$ independently are tert-butyl, halo, $C_{1-6}$ alkoxy, $C_{3-10}$ cycloalkyl, $C_{6-10}$ aryl, or trihalovinyl, wherein said aryl is optionally substituted with 1-3 groups of $R^a$;
each $R^2$ is hydrogen;
$R^3$ and $R^{3a}$ are independently hydrogen, halo, $C_{1-6}$ alkyl, $C_{3-10}$ cycloalkyl, or $C_{6-10}$ aryl, wherein said aryl and alkyl are each optionally substituted with 1-3 groups of $R^a$;
$R^4$ is hydrogen;
$R^a$ represents $C_{1-6}$ alkoxy, $C_{1-6}$ alkyl, $CF_3$, nitro, amino, cyano, $C_{1-6}$ alkylamino, or halogen; and
n represents 1-3.

2. A pharmaceutical composition according to claim 1, wherein in the compound of formula I, or a pharmaceutically acceptable salt thereof, $R^{1a}$ and $R^1$ independently are tert-butyl, 1,2,2-trichlorovinyl, or phenyl.

3. A pharmaceutical composition according to claim 1, wherein in the compound of formula I, or a pharmaceutically acceptable salt thereof, n is 1.

4. A pharmaceutical composition according to claim 1, wherein in the compound of formula I, or a pharmaceutically acceptable salt thereof, $R^{1a}$ and $R^1$ independently are tert-butyl, 1,2,2-trichlorovinyl, or phenyl; and n is 1.

5. A pharmaceutical composition according to claim 4, wherein in the compound of formula I or a pharmaceutically acceptable salt thereof, $R^{1a}$ and $R^1$ are tert-butyl.

6. A pharmaceutical composition according to claim 5, wherein the compound of formula I is 2-(aminomethyl)-3,5-di-tert-butylphenol or a pharmaceutically acceptable salt thereof.

7. A pharmaceutical composition according to claim 6, wherein the compound of formula I is 2-(aminomethyl)-3,5-di-tert-butylphenol hydrochloride.

8. A pharmaceutical composition according to claim 1, wherein the second anti-malarial agent is selected from the group consisting of Chloroquine, Fansidar, Amodiaquine, Quinine, Halofantrine, Mefloquine, Artemether/Artesunate and Malarone.

9. A pharmaceutical composition according to claim 6, wherein the second anti-malarial agent is selected from the group consisting of Chloroquine, Fansidar, Amodiaquine, Quinine, Halofantrine, Mefloquine, Artemether/Artesunate and Malarone.

10. A pharmaceutical composition according to claim 7, wherein the second anti-malarial agent is selected from the group consisting of Chloroquine, Fansidar, Amodiaquine, Quinine, Halofantrine, Mefloquine, Artemether/Artesunate and Malarone.

* * * * *